US008663334B2

(12) United States Patent
Viscardi et al.

(10) Patent No.: US 8,663,334 B2
(45) Date of Patent: Mar. 4, 2014

(54) LATERAL ENTRY INSERT FOR CUP TRIAL

(75) Inventors: David Viscardi, Hoboken, NJ (US); Koustubh Rao, Hackensack, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 8 days.

(21) Appl. No.: 13/484,557

(22) Filed: May 31, 2012

(65) Prior Publication Data
US 2013/0325130 A1    Dec. 5, 2013

(51) Int. Cl.
*A61F 2/40*    (2006.01)
(52) U.S. Cl.
USPC ....................................... 623/19.11
(58) Field of Classification Search
USPC .............. 623/19.11–19.14, 20.28, 20.3, 623/21.11–21.12, 21.17, 20.24, 20.12, 623/20.29, 20.18, 20.2, 20.11–20.15, 21.18, 623/21.19, 21.13–21.15, 23.39–23.46
See application file for complete search history.

(56) References Cited

U.S. PATENT DOCUMENTS

| | | | |
|---|---|---|---|
| 3,102,536 A | 9/1963 | Rose | |
| 3,806,957 A | 4/1974 | Shersher et al. | |
| 3,842,442 A * | 10/1974 | Kolbel | 623/19.12 |
| 3,978,528 A | 9/1976 | Crep | |
| 4,030,143 A | 6/1977 | Elloy et al. | |
| 4,040,131 A | 8/1977 | Gristina | |
| 4,279,041 A | 7/1981 | Buchholz et al. | |
| 4,524,467 A | 6/1985 | DeCarlo, Jr. | |
| D285,968 S * | 9/1986 | Kinnett | D24/155 |
| 4,693,723 A | 9/1987 | Gabard et al. | |
| 4,711,639 A * | 12/1987 | Grundei | 623/20.33 |
| 4,795,468 A * | 1/1989 | Hodorek et al. | 623/20.28 |
| 4,936,853 A * | 6/1990 | Fabian et al. | 623/20.15 |
| 4,944,757 A * | 7/1990 | Martinez et al. | 623/20.15 |
| 5,080,673 A * | 1/1992 | Burkhead et al. | 623/19.11 |
| 5,358,526 A | 10/1994 | Tornier | |
| 5,413,604 A * | 5/1995 | Hodge | 623/20.28 |
| 5,462,563 A | 10/1995 | Shearer et al. | |
| 5,569,263 A | 10/1996 | Hein | |
| 5,609,639 A * | 3/1997 | Walker | 623/20.29 |
| 5,609,644 A * | 3/1997 | Ashby et al. | 623/20.2 |
| 5,658,340 A | 8/1997 | Muller et al. | |
| 5,702,447 A * | 12/1997 | Walch et al. | 623/19.11 |

(Continued)

FOREIGN PATENT DOCUMENTS

DE    10335442 A1    2/2005
DE    202008008565 U1    8/2008

(Continued)

OTHER PUBLICATIONS

Extended European Search Report for Application No. EP12195588 dated Mar. 1, 2013.

(Continued)

*Primary Examiner* — Alvin J. Stewart
(74) *Attorney, Agent, or Firm* — Lerner, David, Littenberg, Krumholz & Mentlik, LLP

(57) ABSTRACT

Trials for a reverse shoulder system are described. The trials generally include an insert housed within a humeral cup. The insert has a proximal end and a distal end, the proximal end having a concave recess therein adapted to receive a glenosphere prosthesis. The distal end of the insert includes a shaft, the shaft is substantially housed within the confines of the humeral cup. A distal end of the humeral cup is inserted in a humeral stem.

17 Claims, 10 Drawing Sheets

(56) References Cited

U.S. PATENT DOCUMENTS

| | | | |
|---|---|---|---|
| 5,702,457 A * | 12/1997 | Walch et al. | 623/19.13 |
| 5,702,470 A * | 12/1997 | Menon | 623/21.12 |
| 5,728,161 A | 3/1998 | Camino et al. | |
| 5,741,335 A | 4/1998 | Gerber et al. | |
| 5,755,801 A * | 5/1998 | Walker et al. | 623/20.21 |
| 5,824,106 A * | 10/1998 | Fournol | 623/21.18 |
| 5,871,545 A * | 2/1999 | Goodfellow et al. | 623/20.28 |
| 5,879,401 A | 3/1999 | Besemer et al. | |
| 5,910,171 A * | 6/1999 | Kummer et al. | 623/18.11 |
| 5,961,555 A | 10/1999 | Huebner | |
| 5,964,808 A * | 10/1999 | Blaha et al. | 623/20.28 |
| 6,033,439 A | 3/2000 | Camino et al. | |
| 6,102,953 A | 8/2000 | Huebner | |
| 6,120,542 A | 9/2000 | Camino et al. | |
| 6,123,728 A * | 9/2000 | Brosnahan et al. | 623/20.24 |
| 6,168,627 B1 | 1/2001 | Huebner | |
| 6,168,628 B1 | 1/2001 | Huebner | |
| 6,193,758 B1 | 2/2001 | Huebner | |
| 6,206,925 B1 * | 3/2001 | Tornier | 623/19.12 |
| 6,210,444 B1 * | 4/2001 | Webster et al. | 623/20.33 |
| 6,217,618 B1 * | 4/2001 | Hileman | 623/20.33 |
| 6,228,119 B1 * | 5/2001 | Ondrla et al. | 623/19.11 |
| 6,228,120 B1 | 5/2001 | Leonard et al. | |
| 6,368,352 B1 | 4/2002 | Camino et al. | |
| 6,379,388 B1 * | 4/2002 | Ensign et al. | 623/20.34 |
| 6,485,520 B1 * | 11/2002 | Hubach et al. | 623/21.13 |
| 6,494,913 B1 | 12/2002 | Huebner | |
| 6,500,208 B1 * | 12/2002 | Metzger et al. | 623/20.28 |
| 6,508,841 B2 | 1/2003 | Martin et al. | |
| 6,514,287 B2 * | 2/2003 | Ondrla et al. | 623/19.13 |
| 6,569,202 B2 * | 5/2003 | Whiteside | 623/20.32 |
| 6,589,282 B2 * | 7/2003 | Pearl | 623/19.14 |
| 6,602,292 B2 * | 8/2003 | Burkinshaw | 623/20.2 |
| 6,673,114 B2 | 1/2004 | Hartdegen et al. | |
| 6,679,916 B1 * | 1/2004 | Frankle et al. | 623/19.12 |
| 6,736,852 B2 | 5/2004 | Callaway et al. | |
| 6,749,637 B1 * | 6/2004 | Bahler | 623/19.14 |
| 6,761,740 B2 | 7/2004 | Tornier | |
| 6,790,234 B1 | 9/2004 | Frankle | |
| 6,800,094 B2 * | 10/2004 | Burkinshaw | 623/20.18 |
| 6,818,019 B2 | 11/2004 | Horber | |
| 6,887,277 B2 | 5/2005 | Rauscher et al. | |
| 6,890,358 B2 * | 5/2005 | Ball et al. | 623/21.13 |
| 6,899,736 B1 * | 5/2005 | Rauscher et al. | 623/19.12 |
| 6,953,478 B2 * | 10/2005 | Bouttens et al. | 623/19.11 |
| 6,969,406 B2 * | 11/2005 | Tornier | 623/19.13 |
| 6,969,407 B2 * | 11/2005 | Klotz et al. | 623/21.12 |
| 6,986,790 B2 | 1/2006 | Ball et al. | |
| 6,986,791 B1 * | 1/2006 | Metzger | 623/20.24 |
| 7,011,686 B2 | 3/2006 | Ball et al. | |
| 7,033,396 B2 * | 4/2006 | Tornier | 623/19.11 |
| 7,097,663 B1 | 8/2006 | Nicol et al. | |
| 7,108,405 B2 | 9/2006 | Matts et al. | |
| 7,108,719 B2 | 9/2006 | Horber | |
| 7,166,132 B2 | 1/2007 | Callaway et al. | |
| 7,169,184 B2 * | 1/2007 | Dalla Pria | 623/19.12 |
| 7,175,663 B1 | 2/2007 | Stone | |
| 7,204,854 B2 * | 4/2007 | Guederian et al. | 623/19.11 |
| 7,238,208 B2 | 7/2007 | Camino et al. | |
| 7,241,314 B1 | 7/2007 | Winslow | |
| 7,297,163 B2 | 11/2007 | Huebner | |
| 7,309,360 B2 | 12/2007 | Tornier et al. | |
| 7,329,284 B2 | 2/2008 | Maroney et al. | |
| 7,357,817 B2 * | 4/2008 | D'Alessio, II | 623/20.15 |
| 7,425,214 B1 | 9/2008 | McCarthy et al. | |
| 7,445,638 B2 | 11/2008 | Beguin et al. | |
| 7,462,197 B2 | 12/2008 | Tornier et al. | |
| 7,465,319 B2 * | 12/2008 | Tornier | 623/19.11 |
| 7,470,287 B2 * | 12/2008 | Tornier et al. | 623/19.13 |
| 7,531,003 B2 * | 5/2009 | Reindel | 623/21.12 |
| 7,544,211 B2 * | 6/2009 | Rochetin | 623/20.34 |
| 7,608,109 B2 * | 10/2009 | Dalla Pria | 623/19.11 |
| 7,611,539 B2 | 11/2009 | Bouttens et al. | |
| 7,621,961 B2 | 11/2009 | Stone | |
| 7,678,150 B2 * | 3/2010 | Tornier et al. | 623/19.13 |
| 7,758,650 B2 * | 7/2010 | Dews et al. | |
| 7,854,768 B2 * | 12/2010 | Wiley et al. | 623/19.14 |
| 7,918,892 B2 | 4/2011 | Huebner | |
| 7,922,769 B2 | 4/2011 | Deffenbaugh et al. | |
| 7,951,204 B2 * | 5/2011 | Chambat et al. | 623/20.33 |
| 7,959,680 B2 | 6/2011 | Stone et al. | |
| 8,002,841 B2 * | 8/2011 | Hasselman | 623/21.18 |
| 8,062,376 B2 | 11/2011 | Shultz et al. | |
| 8,070,820 B2 | 12/2011 | Winslow et al. | |
| 8,092,466 B2 * | 1/2012 | Splieth et al. | 606/102 |
| 8,118,875 B2 * | 2/2012 | Rollet | 623/19.12 |
| 8,118,876 B2 * | 2/2012 | Gupta et al. | 623/21.11 |
| 8,137,407 B2 * | 3/2012 | Todd et al. | 623/20.33 |
| 8,142,510 B2 * | 3/2012 | Lee et al. | 623/20.33 |
| 8,147,557 B2 * | 4/2012 | Lee et al. | 623/20.3 |
| 8,147,558 B2 * | 4/2012 | Lee et al. | 623/20.3 |
| 8,157,866 B2 | 4/2012 | Winslow et al. | |
| 8,206,453 B2 * | 6/2012 | Cooney et al. | 623/21.12 |
| 8,231,683 B2 * | 7/2012 | Lappin et al. | 623/19.11 |
| 8,236,059 B2 | 8/2012 | Stone et al. | |
| 8,241,366 B2 | 8/2012 | Roche et al. | |
| 8,246,687 B2 | 8/2012 | Katrana et al. | |
| 8,303,665 B2 | 11/2012 | Tornier et al. | |
| 8,328,874 B2 * | 12/2012 | Lee | 623/20.3 |
| 8,337,563 B2 | 12/2012 | Roche et al. | |
| 8,361,157 B2 | 1/2013 | Bouttens et al. | |
| 8,366,780 B2 * | 2/2013 | Klawitter et al. | 623/18.11 |
| 8,377,142 B2 * | 2/2013 | Trail et al. | 623/21.17 |
| 8,454,702 B2 * | 6/2013 | Smits et al. | 623/19.11 |
| 2001/0007957 A1 | 7/2001 | Martin et al. | |
| 2002/0120339 A1 | 8/2002 | Callaway et al. | |
| 2002/0128719 A1 * | 9/2002 | Burkinshaw | 623/20.2 |
| 2003/0014119 A1 | 1/2003 | Capon et al. | |
| 2003/0099519 A1 | 5/2003 | Robinson et al. | |
| 2003/0114933 A1 | 6/2003 | Bouttens et al. | |
| 2003/0149486 A1 | 8/2003 | Huebner | |
| 2003/0158605 A1 | 8/2003 | Tornier | |
| 2004/0064188 A1 | 4/2004 | Ball et al. | |
| 2004/0143336 A1 * | 7/2004 | Burkinshaw | 623/20.15 |
| 2004/0143337 A1 * | 7/2004 | Burkinshaw | 623/20.18 |
| 2004/0186579 A1 | 9/2004 | Callaway et al. | |
| 2004/0210317 A1 | 10/2004 | Maroney et al. | |
| 2004/0220674 A1 | 11/2004 | Pria | |
| 2004/0236428 A1 * | 11/2004 | Burkinshaw et al. | 623/20.15 |
| 2004/0267370 A1 | 12/2004 | Ondrla | |
| 2005/0085921 A1 * | 4/2005 | Gupta et al. | 623/21.13 |
| 2005/0113931 A1 | 5/2005 | Horber | |
| 2005/0128755 A1 | 6/2005 | Matts et al. | |
| 2005/0137709 A1 * | 6/2005 | Klotz et al. | 623/21.12 |
| 2005/0143829 A1 | 6/2005 | Ondrla et al. | |
| 2005/0256583 A1 | 11/2005 | Bouttens et al. | |
| 2005/0278030 A1 | 12/2005 | Tornier et al. | |
| 2005/0278032 A1 | 12/2005 | Tornier et al. | |
| 2005/0288681 A1 | 12/2005 | Klotz et al. | |
| 2005/0288791 A1 | 12/2005 | Tornier et al. | |
| 2006/0004462 A1 * | 1/2006 | Gupta | 623/21.13 |
| 2006/0020344 A1 | 1/2006 | Shultz et al. | |
| 2006/0030946 A1 * | 2/2006 | Ball et al. | 623/21.13 |
| 2006/0036329 A1 * | 2/2006 | Webster et al. | 623/20.33 |
| 2006/0052875 A1 * | 3/2006 | Bernero et al. | 623/20.33 |
| 2006/0069445 A1 | 3/2006 | Ondrla et al. | |
| 2006/0129247 A1 | 6/2006 | Brown et al. | |
| 2006/0142872 A1 | 6/2006 | Klotz et al. | |
| 2006/0161260 A1 * | 7/2006 | Thomas et al. | 623/21.12 |
| 2006/0200247 A1 | 9/2006 | Charrois | |
| 2006/0200248 A1 | 9/2006 | Beguin et al. | |
| 2006/0229730 A1 * | 10/2006 | Railey et al. | 623/21.18 |
| 2007/0050040 A1 | 3/2007 | Guederian et al. | |
| 2007/0078519 A1 | 4/2007 | Klotz | |
| 2007/0112430 A1 * | 5/2007 | Simmen et al. | 623/19.14 |
| 2007/0118230 A1 | 5/2007 | Callaway et al. | |
| 2007/0156246 A1 | 7/2007 | Meswania et al. | |
| 2007/0173945 A1 | 7/2007 | Wiley et al. | |
| 2007/0179624 A1 | 8/2007 | Stone et al. | |
| 2007/0225820 A1 * | 9/2007 | Thomas et al. | 623/21.12 |
| 2007/0243045 A1 | 10/2007 | Gaska | |
| 2007/0244563 A1 | 10/2007 | Roche et al. | |
| 2008/0221622 A1 | 9/2008 | Triplett et al. | |
| 2008/0228281 A1 | 9/2008 | Forrer et al. | |

(56) References Cited

U.S. PATENT DOCUMENTS

| | | | |
|---|---|---|---|
| 2008/0243261 A1* | 10/2008 | Wyss et al. | 623/20.33 |
| 2008/0243262 A1* | 10/2008 | Lee | 623/20.33 |
| 2008/0275507 A1 | 11/2008 | Triplett et al. | |
| 2008/0294268 A1 | 11/2008 | Baum et al. | |
| 2009/0099662 A1* | 4/2009 | Splieth et al. | 623/19.14 |
| 2009/0149961 A1 | 6/2009 | Dallmann | |
| 2009/0164021 A1 | 6/2009 | Dallmann | |
| 2009/0171462 A1* | 7/2009 | Poncet et al. | 623/19.12 |
| 2009/0192621 A1 | 7/2009 | Winslow et al. | |
| 2009/0210065 A1 | 8/2009 | Nerot et al. | |
| 2009/0216332 A1* | 8/2009 | Splieth et al. | 623/19.14 |
| 2009/0281630 A1 | 11/2009 | Delince et al. | |
| 2010/0023068 A1 | 1/2010 | Bouttens et al. | |
| 2010/0049327 A1* | 2/2010 | Isch et al. | 623/19.12 |
| 2010/0087927 A1 | 4/2010 | Roche et al. | |
| 2010/0161065 A1 | 6/2010 | Williams, Jr. et al. | |
| 2010/0161066 A1 | 6/2010 | Iannotti et al. | |
| 2010/0222886 A1* | 9/2010 | Wiley et al. | 623/19.13 |
| 2010/0228352 A1 | 9/2010 | Courtney, Jr. et al. | |
| 2011/0112650 A1* | 5/2011 | Masini | 623/20.15 |
| 2011/0153023 A1 | 6/2011 | Deffenbaugh et al. | |
| 2011/0196491 A1 | 8/2011 | Huebner | |
| 2012/0029647 A1 | 2/2012 | Winslow et al. | |
| 2012/0191201 A1 | 7/2012 | Smits et al. | |
| 2012/0209392 A1 | 8/2012 | Angibaud et al. | |
| 2012/0221112 A1 | 8/2012 | Lappin | |
| 2012/0239159 A1* | 9/2012 | Metzger et al. | 623/20.28 |
| 2012/0253467 A1 | 10/2012 | Frankle | |
| 2012/0303130 A1* | 11/2012 | Winslow et al. | 623/19.12 |
| 2012/0330428 A1* | 12/2012 | Splieth et al. | 623/19.14 |
| 2013/0006369 A1* | 1/2013 | Wiley et al. | 623/19.14 |
| 2013/0006374 A1* | 1/2013 | Le Couedic et al. | 623/20.28 |
| 2013/0060341 A1* | 3/2013 | Tornier et al. | 623/19.13 |
| 2013/0090736 A1* | 4/2013 | Katrana et al. | 623/19.13 |
| 2013/0144393 A1* | 6/2013 | Mutchler et al. | 623/19.11 |
| 2013/0144394 A1* | 6/2013 | Hassler et al. | 623/19.11 |
| 2013/0150973 A1* | 6/2013 | Splieth et al. | 623/19.11 |
| 2013/0150975 A1* | 6/2013 | Iannotti et al. | 623/19.11 |
| 2013/0197650 A1* | 8/2013 | Smits et al. | 623/19.13 |
| 2013/0197651 A1* | 8/2013 | McDaniel et al. | 623/19.13 |
| 2013/0197652 A1* | 8/2013 | Ekelund et al. | 623/19.14 |
| 2013/0204375 A1* | 8/2013 | Winslow et al. | 623/19.13 |
| 2013/0245775 A1* | 9/2013 | Metcalfe | 623/19.12 |

FOREIGN PATENT DOCUMENTS

| | | |
|---|---|---|
| EP | 1314407 A1 | 5/2003 |
| EP | 1520560 | 4/2005 |
| EP | 1656910 A1 | 5/2006 |
| EP | 2047827 A1 | 4/2009 |
| EP | 2201912 A1 | 6/2010 |
| FR | 2689756 | 10/1993 |
| FR | 2699400 | 6/1994 |
| GB | 2001247 | 1/1979 |
| GB | 2405346 A | 3/2005 |
| WO | 0147442 A1 | 7/2001 |
| WO | 2005032430 | 4/2005 |
| WO | 2007031575 A1 | 3/2007 |
| WO | 2007039820 | 4/2007 |
| WO | 2007084939 | 7/2007 |
| WO | 2008000928 A2 | 1/2008 |

OTHER PUBLICATIONS

Delta Reverse Shoulder System, Surgical Technique, DePuy 2004.
European Search Report, EP 10156704, dated Jun. 14, 2010.
Mode Operatoire, Operative Technique, Arrow, date not known.
Reverse Shoulder Prosthesis, Surgical Technique, Encore, 2005.
Trabecular Metal Reverse Shoulder System, Zimmer, date not known.
Extended European Search Report for Application No. 12183703 dated Jan. 30, 2013.
Extended European Search Report for Application No. EP13169019 dated Jul. 26, 2013.

* cited by examiner

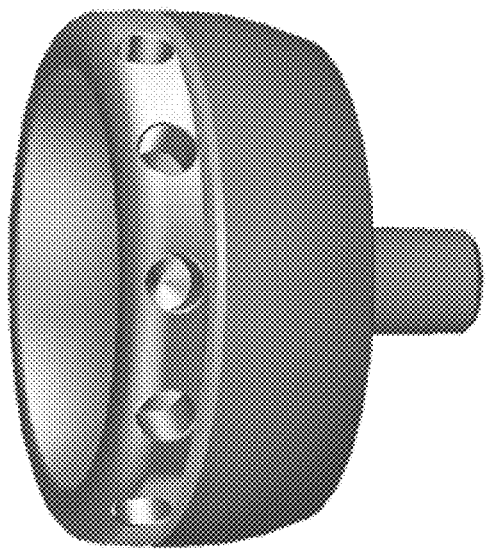
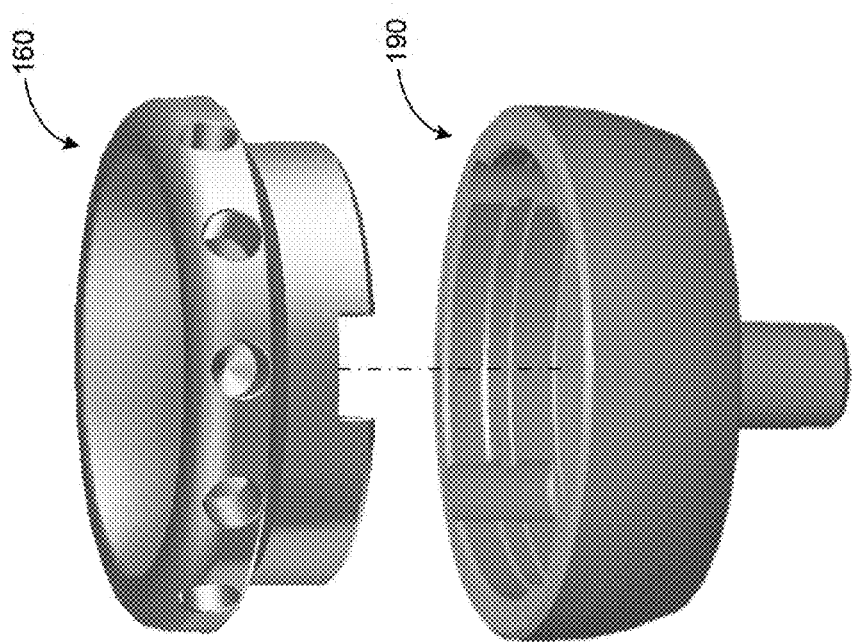
FIG. 6B
FIG. 6A

LATERAL ENTRY INSERT FOR CUP TRIAL

FIELD OF THE INVENTION

The present invention relates to a shoulder trial for reverse shoulder arthroplasty (RSA), and in particular it relates to such a trial including an insert and humeral cup that are configured to engage one another by sliding the insert from a transverse or lateral direction into engagement with the humeral cup.

BACKGROUND OF THE INVENTION

The successful outcome of RSA depends greatly on proper soft tissue tension in the shoulder joint. The stability of the shoulder joint is generally maintained from significant deltoid tension holding this ball and socket joint together. Some RSA systems require the surgeon to use a trial and error approach in establishing proper soft tissue tension. Such approaches often take several attempts before adequate stability is achieved.

When performing a trialing step in a reverse shoulder procedure, one important aspect is to determine the correct height of the humeral insert implant that will ultimately be chosen for the patient. A series of humeral insert trials with varying heights is normally utilized to determine the correct height for the implant. By using thicker or thinner insert trials the soft tissue tension and joint range of motion can be optimized for the patient.

Such trialing procedures generally include selecting a first trial insert, installing it into other parts of the shoulder system, reducing the joint, and then checking the joint for soft tissue tension and range of motion. The joint is then dislocated, and if the correct humeral insert implant height has been determined the reverse shoulder implantation proceeds. When the correct trial is determined, the soft tissue tension is significant, requiring the surgeon to apply extreme force to the humerus and surrounding soft tissues to reduce the joint. If no additional damage is done during this reduction process, the joint must then be dislocated to allow the surgeon to implant a joint replacement prosthesis.

If the correct humeral insert height has not yet been determined, then a second trial insert with a different thickness than the first trial is selected. The second trial insert is installed and the joint is assessed. As a result of the trialing procedure, the reverse shoulder joint can be reduced and dislocated multiple times.

Traditionally, each time the reverse shoulder joint is reduced and dislocated, the soft tissue has to be stretched in order for the glenosphere to be placed in or removed from the humeral insert. This stretching of the soft tissue can lead to joint instability and increased recovery time for the patient.

BRIEF SUMMARY OF THE INVENTION

The trial assembly of the present invention includes at least a trial cup and a trial insert. In one embodiment of the present invention, a recess or guide track of an insert trial is slid over a centering member or positive stop pin on a cup trial. Flanges on the cup trial are received within a groove of the insert trial as the guide track is slid over the centering member. After the centering member is located adjacent the deepest part of the guide track, the insert trial is preferably rotated in either a clockwise or counterclockwise direction substantially locking the lateral and vertical movement of the insert trial with respect to the cup trial. The rotational movement of the insert trial with respect to the cup trial can still occur.

The lateral engagement and disengagement of the insert trial and insert cup allows any size insert trial and cup to be used during the trialing process in contrast to having to reduce and distract the trials from each other prior to and after use.

In the past, there have been issues with achieving appropriate tensioning during RSA due to difficulties in inserting and removing the trials from between the humeral components and the glenosphere component on the glenoid. The trial assembly of the present invention provides a way of reducing and dislocating the joint without any temporary increase in joint tension that is usually experienced when reducing the ball up, over, and into the insert trial socket.

In accordance with a first aspect of the present invention is a trial assembly comprising a trial cup and a trial insert. The trial cup has a distal end surface and a proximal end surface, the proximal end surface including first and second flanges and a centering member protruding outwardly therefrom. The trial insert includes a proximal end portion and a shaft portion having a distal end, the shaft portion having a groove around an outer circumference thereof and a recess in the distal end thereof. The trial insert is operatively coupled to the trial cup when the centering member is received in the recess of the trial insert and an engagement member on each of the first and second flanges is received within the groove of the trial insert.

In one embodiment of this first aspect, the trial assembly further includes an elongate shaft having proximal and distal ends, the distal end surface of the trial cup adapted to lie adjacent to the proximal end of the elongate shaft when the trial cup is coupled to the elongate shaft.

In another embodiment of this first aspect, the first and second flanges of the trial cup extend outwardly from at least a portion of an outer circumference of the proximal end surface of the trial cup.

In yet another embodiment of this first aspect, the recess of the trial insert begins at the outer circumference of the shaft portion and terminates adjacent a central axis of the trial insert. When a longitudinal axis of the centering member is collinear with the central axis of the trial insert, the trial insert may be rotated in a radial direction about the central axis thereof. Further, rotating the trial insert 90° in either a first or second radial direction about a central axis thereof results in lateral locking of the trial insert and trial cup such that the trial insert and trial cup cannot be uncoupled by offsetting the longitudinal axis of the centering member of the trial cup and central axis of the trial insert. Further still, rotating the trial insert another 90° in either a first or second radial direction about the central axis thereof results in lateral unlocking of the trial insert and trial cup such that the trial insert and trial cup can be uncoupled by offsetting the longitudinal axis of the centering member of the trial cup and central axis of the trial insert.

In still yet another embodiment of this first aspect, the proximal end portion of the trial insert has a concave recess therein.

In still yet another embodiment of this first aspect, the proximal end portion of the insert includes an outer face having a plurality of calibration marks arranged thereon. The calibration marks are preferably located at 90° increments.

In still yet another embodiment of this first aspect, an outer face of the insert includes a plurality of attachment locations adapted to be engaged by an adjustment tool for rotating the trial insert about the central axis thereof.

In still yet another embodiment of this first aspect, the proximal end surface of the cup has a marker thereon.

In still yet another embodiment of this first aspect, a size or height of the trial assembly is measured by the axial distance between a proximal end surface of the trial insert and the distal end surface of the trial cup.

In accordance with a second aspect of the present invention is a trial assembly comprising a trial cup and a trial insert. The trial cup has a distal end surface and a proximal end surface, the proximal end surface including first and second flanges about a circumference thereof and a centering member protruding outwardly along a central longitudinal axis thereof. The trial insert includes a proximal end portion and a shaft portion having a distal end, the shaft portion having a groove around an outer circumference thereof and a recess in the distal end thereof, the recess begins about a circumference of the shaft and terminates adjacent a central longitudinal axis of the trial insert. The trial insert is operatively coupled to the trial cup when the centering member is received in the recess of the trial insert such that the central longitudinal axes of the centering member and trial insert are collinear and a portion of each of the first and second flanges is received at least partially within the groove of the trial insert.

In one embodiment of this second aspect, when the central longitudinal axes of the centering member and trial insert are collinear, the trial insert may be rotated in a radial direction about the central longitudinal axis of the centering member. Further, rotating the trial insert 90° in either a first or second radial direction about a central axis thereof results in lateral locking of the trial insert and trial cup such that the trial insert and trial cup cannot be uncoupled by offsetting the longitudinal axis of the centering member of the trial cup and central axis of the trial insert. Further still, rotating the trial insert another 90° in either a first or second radial direction about the central axis thereof results in lateral unlocking of the trial insert and trial cup such that the trial insert and trial cup can be uncoupled by offsetting the longitudinal axis of the centering member of the trial cup and central axis of the trial insert.

In another embodiment of this second aspect, a size or height of the trial assembly is measured by the axial distance between a proximal end surface of the trial insert and the distal end surface of the trial cup.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 6A is an exploded view of an implant cup and trial insert.

FIG. 6B is an assembled view of the implant cup and trial insert shown in FIG. 6A.

DETAILED DESCRIPTION

Figure 1:
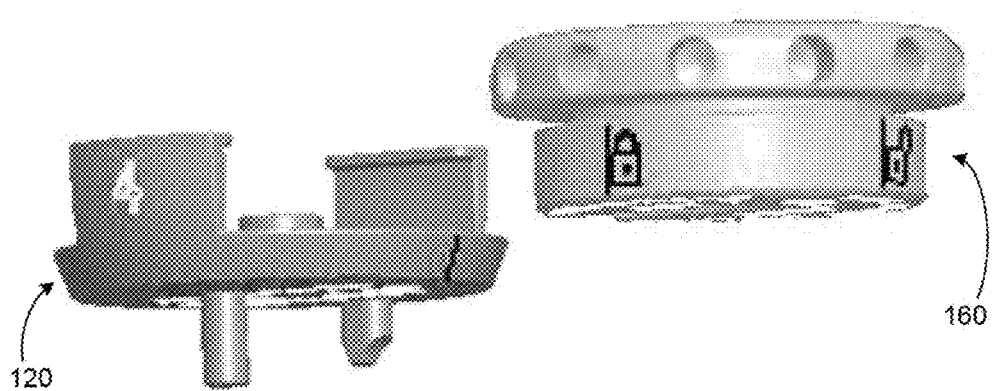
FIG. 1 is an exploded perspective view of one embodiment of a trial assembly of the present invention including a trial cup and a trial insert.
Figure 2:
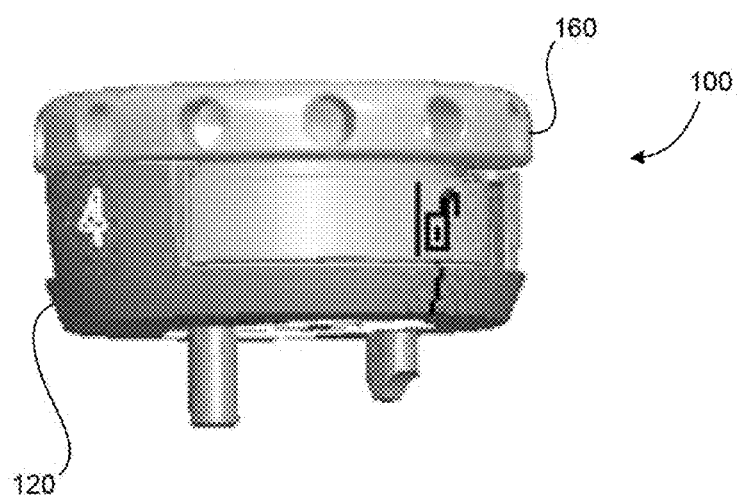
FIG. 2 is an assembled perspective view of one embodiment of a trial assembly of the present invention including the trial cup and the trial insert of FIG. 1.
Figure 3:
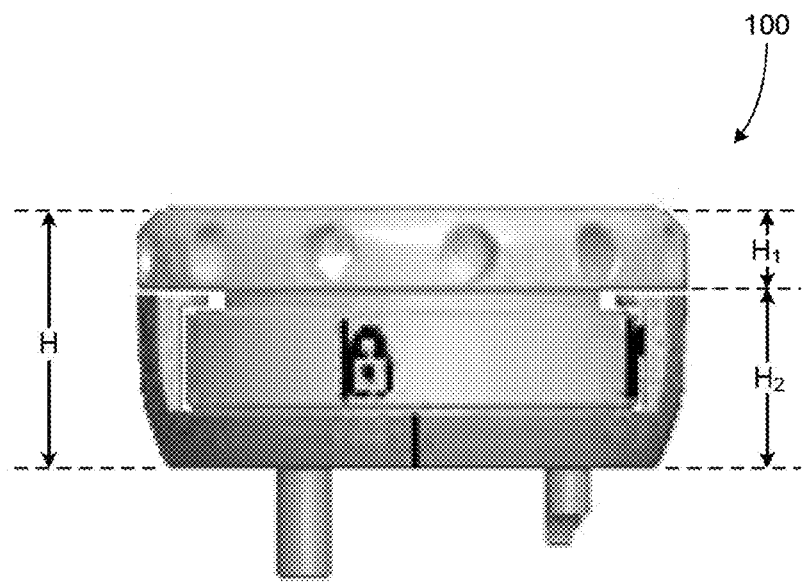
FIG. 3 is a side view of the trial assembly shown in FIG. 2.

Referring to FIGS. 1-3, there is shown an embodiment of a trial assembly of the present invention designated generally by reference numeral 100. As shown in those figures, trial assembly 100 includes a trial cup 120 and a trial insert 160.

Figure 4A:
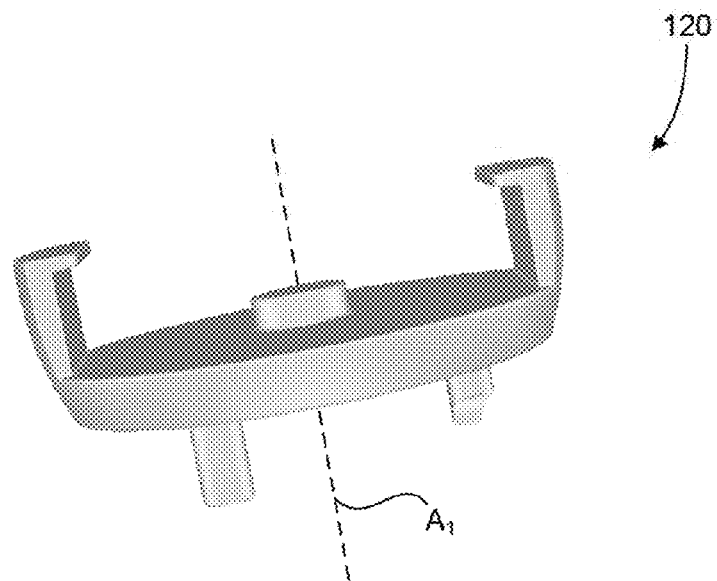
FIG. 4A is a perspective view of one embodiment of a trial cup of the present invention.
Figure 4B:
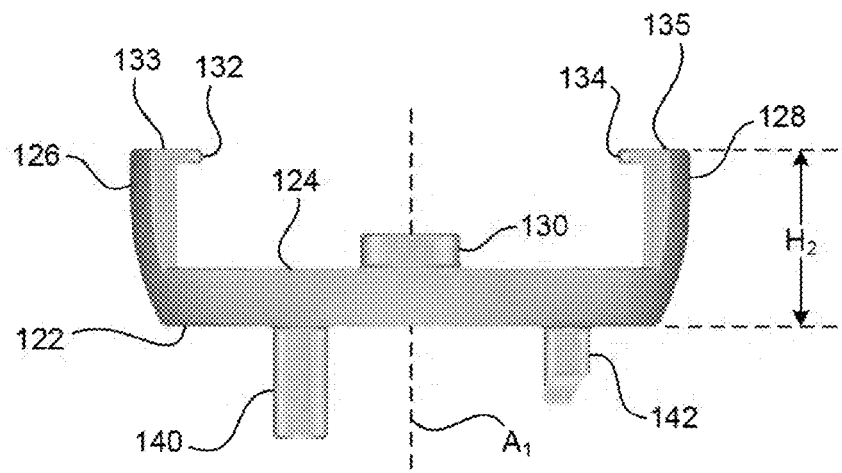
FIG. 4B is a side view of the trial cup shown in FIG. 4A.
Figure 4C:
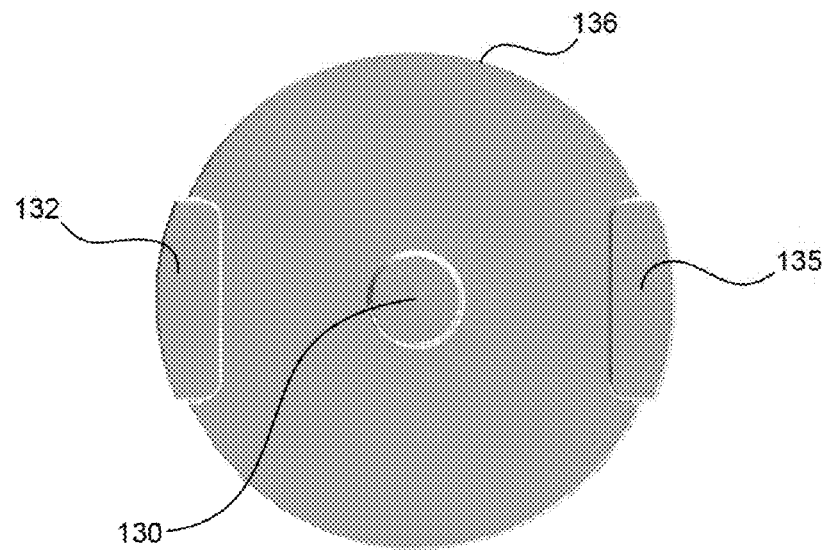
FIG. 4C is a top view of the trial cup shown in FIG. 4A.
Figure 4D:
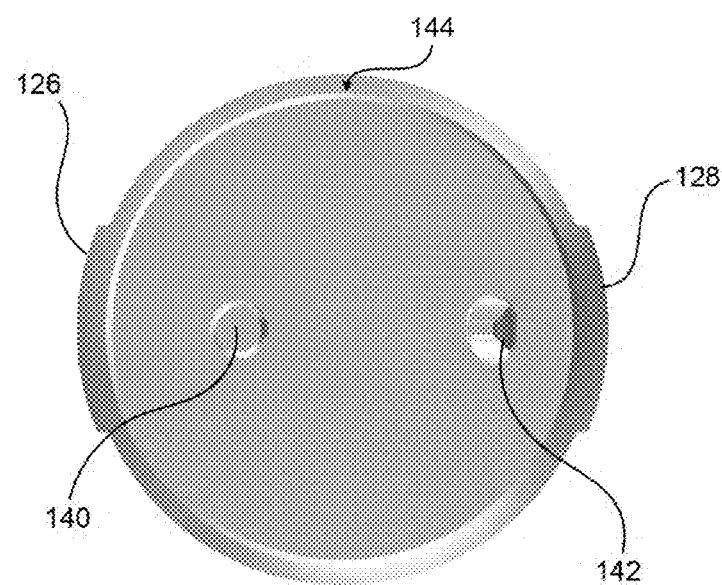
FIG. 4D is a bottom view of the trial cup shown in FIG. 4A.

FIGS. 4A-D show an embodiment of trial cup 120. As shown in these figures, trial cup 120 includes a distal end surface 122 and a proximal end surface 124. Proximal end surface 124 includes first and second flanges 126, 128 and a centering member 130 protruding outwardly therefrom. Proximal end surface 124 preferably includes a marker 144 thereon as shown in FIG. 4D.

First and second flanges 126, 128 preferably extend outwardly from at least a portion of an outer circumference 136 of proximal end surface 124 of trial cup 120. First and second flanges 126, 128 include an engagement member 132, 134 respectively. Engagement members 132, 134 preferably extend outwardly from inner surfaces of first and second flanges 126, 128. Engagement members 132, 134 preferably include a top surface 133, 135, respectively. As seen in FIGS. 4A and 4B, axis A1 is a central longitudinal axis through centering member 130 and is also is a central longitudinal axis for trial cup 120.

Protruding outwardly from distal end surface 122 of trial cup are preferably first and second coupling members 140, 142. Coupling members 140, 142 are configured to engage first and second recesses in a stem or elongate shaft (not shown) in order to couple the stem and trial cup 120.

FIGS. 5A-D show an embodiment of trial insert 160. As shown in these figures, trial insert 160 includes a proximal end portion 162 and a shaft portion 164 having a distal end 166. Shaft portion 164 has a groove 168 around an outer circumference 170 thereof and a recess 172 in the distal end 166 thereof. Recess 172 of trial insert 160 preferably begins at outer circumference 170 of shaft portion 164 and preferably terminates adjacent a central axis A2 of the trial insert 160.

Figure 5A:
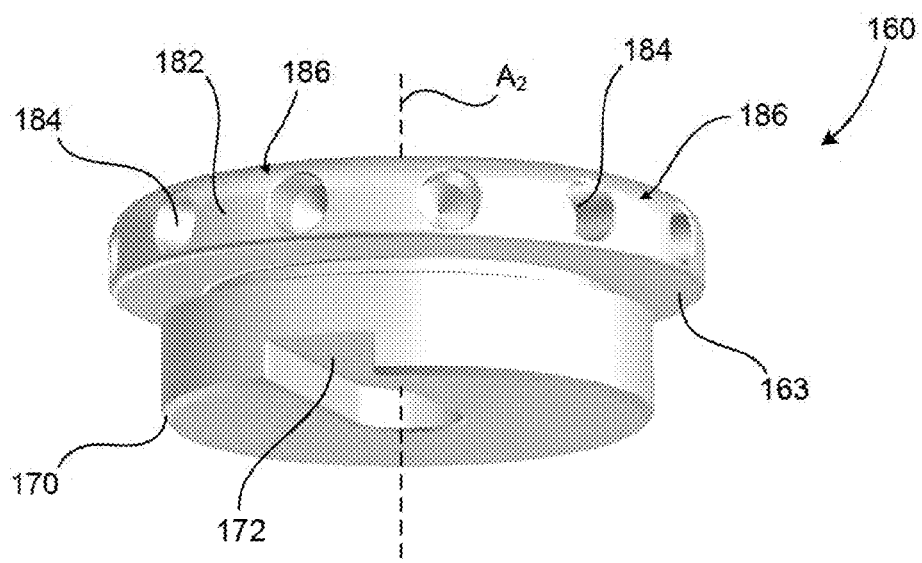
FIG. 5A is a perspective view of one embodiment of a trial insert of the present invention.
Figure 5B:
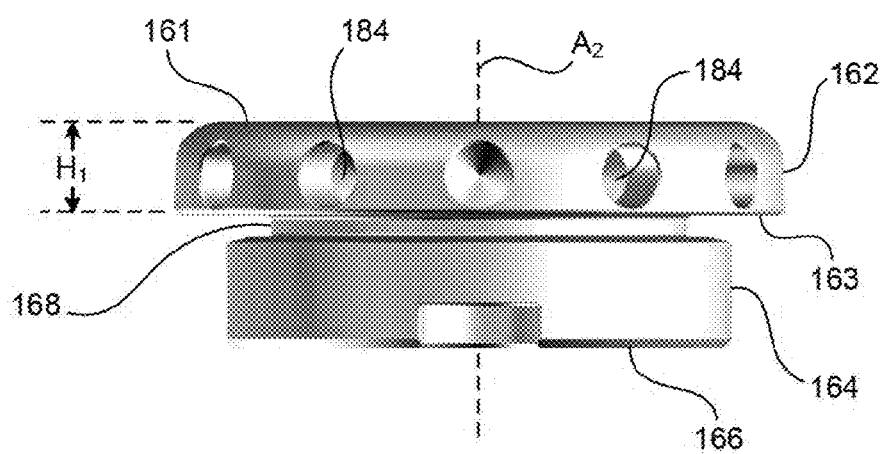
FIG. 5B is a side view of the trial insert shown in FIG. 5A.
Figure 5C:
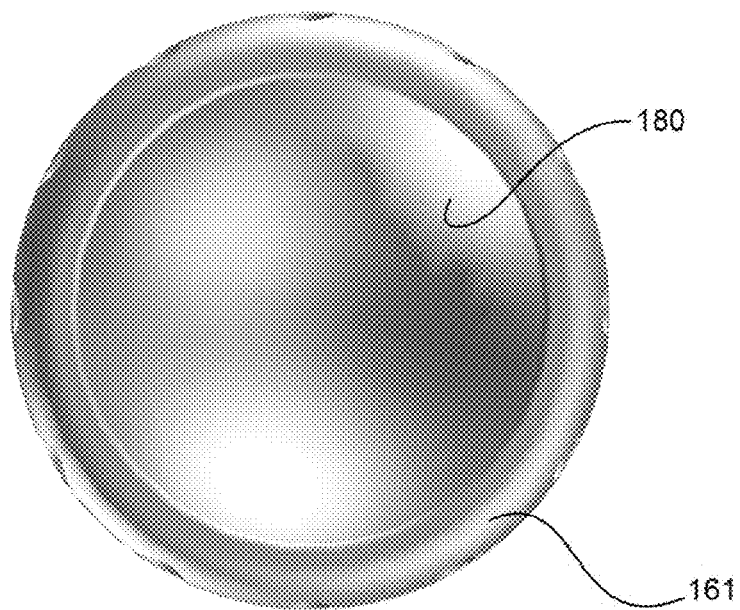
FIG. 5C is a top view of the trial insert shown in FIG. 5A.
Figure 5D:
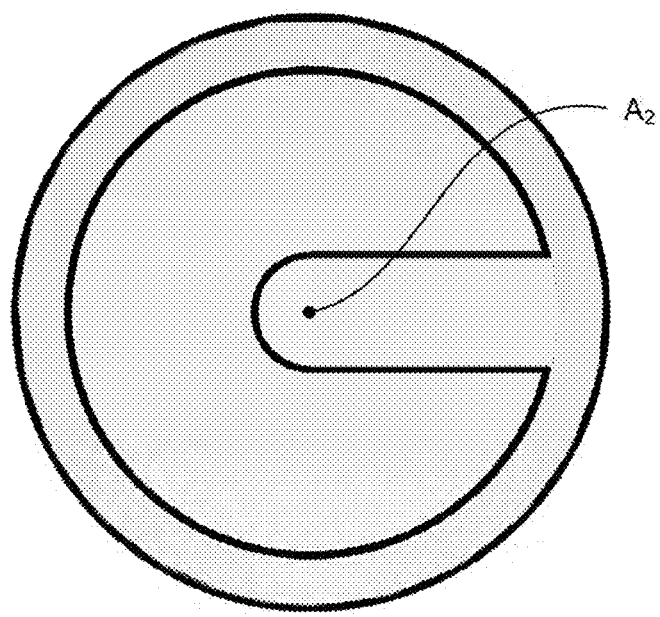
FIG. 5D is a bottom view of the trial insert shown in FIG. 5A.

As shown in FIG. 5C, proximal end portion 162 of trial insert 160 has a concave recess 180 therein. Concave recess 180 is adapted to contact and house a portion of a glenosphere (not shown). Proximal end portion 162 of trial insert 160 includes an outer face 182 preferably having a plurality of attachment locations 184 and calibration marks 186 arranged thereon. The attachment locations 184 are preferably located at 30° increments about outer face 182, but may be located from one another at increments greater or less than 30°. The calibration marks 186 are preferably located at 90° increments about outer face 182, but may be located from one another at increments greater or less than 90°. Attachment locations 184 are adapted to be engaged by an adjustment tool (not shown) for rotating the trial insert 160 about central axis A2 thereof.

A reverse shoulder implant typically consists of five components: a humeral stem, a humeral cup, a humeral insert, a glenosphere baseplate, and a glenosphere. The embodiment of trial assembly 100 shown in FIGS. 1-3 includes two distinct components, namely trial cup 120 and trial insert 160, which are designed to allow a surgeon to determine which size humeral cup and humeral insert are needed to provide a shoulder joint with optimal deltoid tension in a RSA procedure. Both trial cup 120 and trial insert 160 are designed to work with other components or parts of a reverse shoulder implant and instrumentation thereof as part of a complete system in order to give a surgeon intraoperative flexibility and to accommodate surgeon preference. In addition, the design of trial cup 120 and trial insert 160 allows trial insert 160 to slide into trial cup 120 from a direction substantially transverse to the direction of trial cup axis A1, which minimizes soft tissue stretching when reducing or dislocating a reverse shoulder during a trialing process, and gives a surgeon the ability to perform a trialing procedure using instruments only or some combination of instruments and implants.

The design of trial assembly 100 overcomes the challenge of soft tissue stretching when reducing or dislocating a joint by allowing the trial humeral insert to slide into the trial humeral cup at an angle substantially transverse to the axis of the cup. Since the trial insert 160 can enter the trial cup 120 at a transverse angle to trial cup axis A1, reduction or dislocation of the joint can be achieved without the need to pull the glenosphere over the rim of trial insert 160. Soft tissue stretching is therefore minimized.

In one method of the present invention, trial insert 160 is operatively coupled to trial cup 120 when centering member 130 of trial cup 120 is received in recess 172 of trial insert 160 and an engagement member 132, 134 on each of first and second flanges 126, 128 of trial cup 120 is received within groove 168 of trial insert 160. When centering member 130 is located within recess 172 of trial insert 160 and longitudinal axis A1 of centering member 130 is collinear with central axis A2 of trial insert 160, trial insert 160 may be rotated in a radial direction about central axis A2 thereof. The trial insert 160 can be reversibly locked into the trial cup 120 simply by turning the trial insert 160 approximately 15 degrees to approximately 165 degrees after initially engaging the trial insert 160 and trial cup 120. For example, after axes A1, A2 become collinearly oriented, rotating the trial insert 160 approximately 90° in either a first or second radial direction about central axis A2 thereof results in lateral locking of trial insert 160 and trial cup 120 such that trial insert 160 and trial cup 120 cannot be uncoupled by offsetting longitudinal axis A1 of the centering member 130 of trial cup 120 and central axis A2 of trial insert 160. Rotating trial insert 160 approximately another 90° in either a first or second radial direction about central axis A2 thereof results in lateral unlocking of trial insert 160 and trial cup 120 such that trial insert 160 and trial cup 120 can be uncoupled by offsetting longitudinal axis A1 of centering member 130 of trial cup 120 and central axis A2 of trial insert 160.

When operatively coupled, trial insert 160 can be rotated with respect to trial cup 120 by using an attachment tool having an end that can be received in attachment locations 184. A surgeon can estimate the amount of degrees that trial insert 160 has been rotated with respect to trial cup 120 by visualizing the movement of calibration marks 186 located on outer face 182 or by visualizing the movement of calibration marks 186 with respect to marker 144 located on proximal end surface 124 of trial cup 120.

As shown in FIGS. 3 and 5B, a first height H1 is defined by the planar distance between a proximal end surface 161 and distal surface 163 of proximal end portion 162 of trial insert 160. As shown in FIGS. 3 and 4B, a second height H2 is defined by the planar distance between a top surface 133, 135 of engagement members 132, 134 and distal end surface 122 of trial cup 120. A size or height H of trial assembly 100 is measured by the axial or planar distance between proximal surface 161 of trial insert 160 and distal end surface 122 of trial cup 120 as shown in FIG. 3.

During the trial process, a surgeon may use one or more of a plurality of different sized trial cups and inserts. Each insert 160 preferably has a first height H1 between 4 mm and 12 mm in increments of 2 mm as shown in the chart below. A surgeon may then use one or more of a plurality of different sized trial cups 120. Each cup 120 preferably has a second height H2 that is either 4 mm or 10 mm as shown in the chart below. The following chart is a non-limiting example of the different sized trial inserts 160, trial cups 120 and the resultant total height H (8 mm, 10 mm, 12 mm, 14 mm, 16 mm, 18 mm, 20 mm and 22 mm) that can be achieved when trial inserts 160 and trial cups 120 are assembled and used during the trialing process:

|  | 4 mm Insert | 6 mm Insert | 8 mm Insert | 10 mm Insert | 12 mm Insert |
| --- | --- | --- | --- | --- | --- |
| 4 mm Cup | 8 | 10 | 12 | 14 | 16 |
| 10 mm Cup | 14 | 16 | 18 | 20 | 22 |

Figures 7A, 7B:
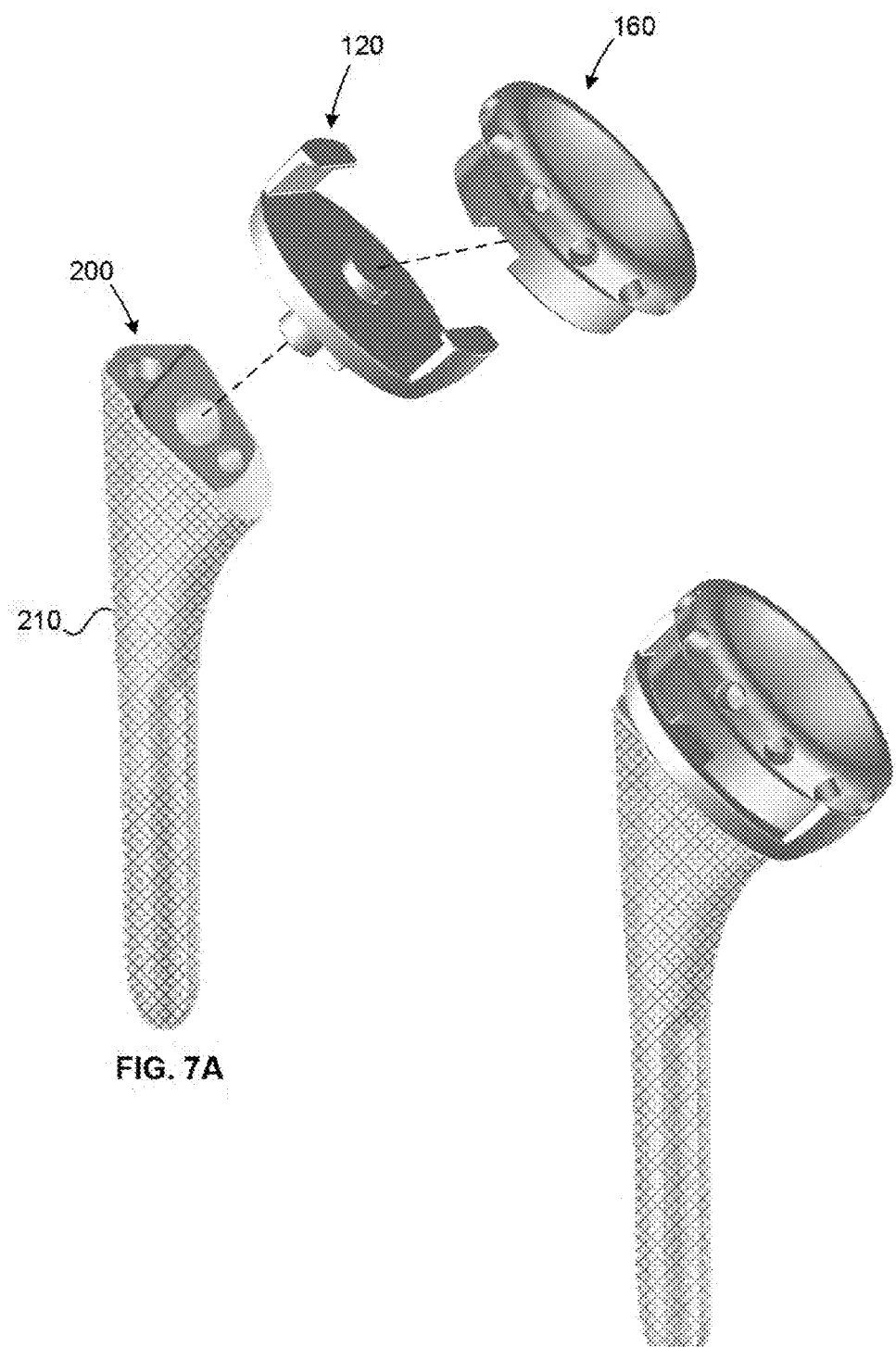
FIG. 7A is an exploded view of a broach, trial cup and trial insert.
FIG. 7B is an assembled view of the broach, cup and trial insert shown in FIG. 7A.
Figures 8A, 8B:
FIG. 8A is an exploded view of an implant stem, implant cup and trial insert.
FIG. 8B is an assembled view of the implant stem, implant cup and trial insert shown in FIG. 8A.
Figure 9A:
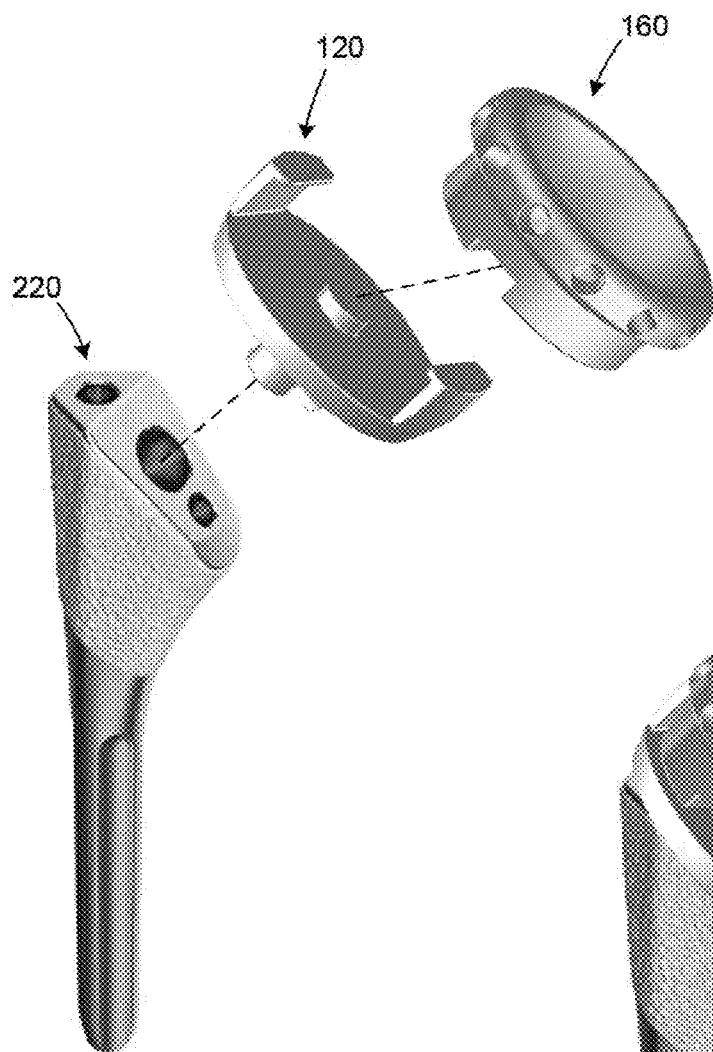
FIG. 9A is an exploded view of an implant stem, trial cup and trial insert.
Figure 9B:
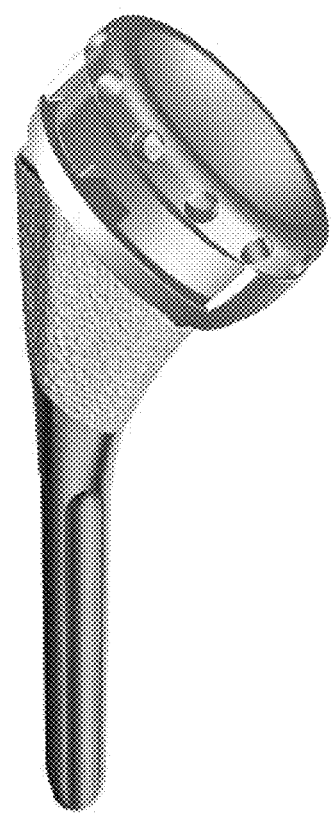
FIG. 9B is an assembled view of the implant stem, trial cup and trial insert shown in FIG. 9A.

The design of trial assembly 100 overcomes the challenge of having one system allowing multiple intraoperative options with regard to trialing by allowing the trial cup 120 to be connected to either a broach 200 as shown in FIGS. 7A-B or humeral stem implant 220 as shown in FIGS. 9A-B, and also by allowing the trial insert 160 to be able to be connected to either trial cup 120 or implant cup 190 as shown in FIGS. 6A-6B and 8A-8B.

Surgeon preferences result in implants and instruments being used in different combinations. For example, some surgeons prefer to perform the trialing procedure off of a broach including cutting portions 210 such as teeth, for example, as shown in FIGS. 7A-7B used to create a cavity into which a humeral stem implant will eventually be placed. Some surgeons instead prefer to trial off of the humeral stem itself as shown in FIGS. 8A-8B and 9A-9B. As a result, it is advantageous for any trial humeral cup to be able to be connected to both the broach and humeral stem implant. Likewise, some surgeons prefer to perform the trialing procedure off of a trial humeral cup and some surgeons prefer to trial off of the humeral cup implant. Therefore it is advantageous for the humeral insert trial to be able to be connected to both the trial humeral cup and the humeral cup implant.

The same trial insert 160 that can be slid into engagement with trial cup 120 at an angle transverse to trial cup axis A1 can also be dropped into a humeral cup implant along an axis coincident with both the humeral cup implant and trial insert 160. The attachment mechanisms that permit a connection between an implant component and a trial do not compromise the integrity of the attachment mechanisms used to connect two implant components. Such a design allows a surgeon to trial off of an implant with confidence that the trialing procedure is not damaging the implant attachment mechanisms which could possibly compromise the performance of the implant after final assembly.

In other embodiments, trial insert 160 may be able to engage trial cup 120 by sliding in a lateral direction into engagement with the trial cup 120, with trialing occurring as the trial insert 160 expands away from and collapses toward trial cup 120. For example, groove 168 of trial insert 160 may be in the form of a helical groove about shaft portion 164. The motion of trial insert along axis A1 of trial cup 120 may be guided by the interaction between the helical groove and an engagement member 133 or 125, for example. In such an embodiment, centering member 130 of trial cup 120 will have a larger height and recess 172 of trial insert 160 will have a greater depth such that the centering member 130 will remain at least partially within recess 172 as trial insert 160 expands and collapses with respect to trial cup 120.

The interaction of the helical groove and engagement member occurs much like that shown in U.S. Pat. Pub. No. 2009/0099662 titled "Expandable Reverse Shoulder Trial," the disclosure of which is hereby incorporated by reference in its entirety. When trial insert 160 first becomes operatively engaged to trial cup 120, trial insert 160 may then be rotated into a fully collapsed or neutral position. Such a device may allow a surgeon to easily reduce the shoulder joint.

Preferably, trial insert 160 may then be advanced to a position where optimal deltoid tension is achieved. At this position, the trial insert 160 and trial cup 120 are preferably calibrated such that the surgeon may determine a liner thickness corresponding to a dialed position of the insert with respect to the cup.

Preferably, the surgeon may then easily collapse the trial back to the neutral position and simply dislocate the joint. Further, the trial may also be preferably expanded prior to joint reduction and collapsed prior to joint dislocation repeatedly, depending on surgeon preference. Once the trial has been optimized, a surgeon preferably records the dialed position of the expanded trial. This measurement should preferably be the liner thickness. If this measurement does not correspond to the size of a particular liner in the system, the surgeon may select a next larger sized liner. At this time, the surgeon may remove the trial and then implant a prosthesis including a humeral cup and the selected liner.

The embodiments described herein have applications in RSA as well as any other ball and socket joints that require dislocation and reduction, such as hip joints for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A trial assembly comprising:
a trial cup having a distal end surface and a proximal end surface, the proximal end surface including first and second flanges and a centering member protruding outwardly about a longitudinal axis of the trial cup; and
a trial insert including a proximal end portion and a shaft portion having a distal end, the shaft portion having a groove around an outer circumference thereof and a recess in the distal end thereof,
wherein the trial insert may be rotated in a radial direction about the longitudinal axis of the trial cup when the centering member is slidably received in the recess of the trial insert in a direction orthogonal to the longitudinal axis of the trial cup and an engagement member on each of the first and second flanges is received within the groove of the trial insert.

2. The trial assembly of claim 1, further including an elongate shaft having proximal and distal ends, the distal end surface of the trial cup adapted to lie adjacent to the proximal end of the elongate shaft when the trial cup is coupled to the elongate shaft.

3. The trial assembly of claim 1, wherein the first and second flanges extend outwardly from at least a portion of an outer circumference of the proximal end surface of the trial cup.

4. The trial assembly of claim 1, wherein the recess of the trial insert begins at the outer circumference of the shaft portion and terminates adjacent a central axis of the trial insert.

5. The trial assembly of claim 4, wherein when a longitudinal axis of the centering member is collinear with the central axis of the trial insert, the trial insert may be rotated in a radial direction about the central axis thereof.

6. The trial assembly of claim 5, wherein rotating the trial insert 90° in either a first or second radial direction about a central axis thereof results in lateral locking of the trial insert and trial cup such that the trial insert and trial cup cannot be uncoupled by offsetting the longitudinal axis of the centering member of the trial cup and central axis of the trial insert.

7. The trial assembly of claim 6, wherein rotating the trial insert another 90° in either a first or second radial direction about the central axis thereof results in lateral unlocking of the trial insert and trial cup such that the trial insert and trial cup can be uncoupled by offsetting the longitudinal axis of the centering member of the trial cup and central axis of the trial insert.

8. The trial assembly of claim 1, wherein the proximal end portion of the trial insert has a concave recess therein.

9. The trial assembly of claim 1, wherein the proximal end portion of the insert includes an outer face having a plurality of calibration marks arranged thereon.

10. The trial assembly of claim 9, wherein the calibration marks are located at 90° increments.

11. The trial assembly of claim 1, wherein an outer face of the insert includes a plurality of attachment locations adapted to be engaged by an adjustment tool for rotating the trial insert about the central axis thereof.

12. The trial assembly of claim 1, wherein the proximal end surface of the cup has a marker thereon.

13. The trial assembly of claim 1, wherein a size of the trial assembly is measured by the axial distance between a proximal end surface of the trial insert and the distal end surface of the trial cup.

14. A trial assembly comprising:
a trial cup having a distal end surface and a proximal end surface, the proximal end surface including first and second flanges about a circumference thereof and a centering member protruding outwardly along a central longitudinal axis thereof; and
a trial insert including a proximal end portion and a shaft portion having a distal end, the shaft portion having a groove around an outer circumference thereof and a recess in the distal end thereof, the recess begins about a circumference of the shaft and terminates adjacent a central longitudinal axis of the trial insert,
wherein the trial insert may be rotated in a radial direction about the central longitudinal axis of the trial cup when the centering member of the trial cup is slidably received in the recess of the trial insert in a direction orthogonal to the central longitudinal axis of the trial cup such that the central longitudinal axes of the trial cup and trial insert are collinear and a portion of each of the first and second flanges is received at least partially within the groove of the trial insert.

15. The trial assembly of claim 14, wherein rotating the trial insert 90° in either a first or second radial direction about the central longitudinal axis thereof results in lateral locking of the trial insert and trial cup such that the trial insert and trial cup cannot be uncoupled by offsetting the central longitudinal axis of the trial cup and central longitudinal axis of the trial insert.

16. The trial assembly of claim 15, wherein rotating the trial insert another 90° in either a first or second radial direction about the central longitudinal axis thereof results in lateral unlocking of the trial insert and trial cup such that the trial insert and trial cup can be uncoupled by offsetting the central longitudinal axis of the trial cup and central longitudinal axis of the trial insert.

17. The trial assembly of claim 14, wherein a size of the trial assembly is measured by the axial distance between a proximal end surface of the trial insert and the distal end surface of the trial cup.

\* \* \* \* \*